United States Patent
Xie et al.

(10) Patent No.: US 7,352,458 B2
(45) Date of Patent: Apr. 1, 2008

(54) SYSTEM AND METHOD FOR HIGH SENSITIVITY VIBRATIONAL IMAGING WITH FREQUENCY MODULATION COHERENT ANTI-STOKES RAMAN SCATTERING ANALYSES

(75) Inventors: Xiaoliang Sunney Xie, Lexington, MA (US); Feruz Ganikhanov, Annandale, NJ (US); Conor Evans, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 11/376,396

(22) Filed: Mar. 15, 2006

(65) Prior Publication Data
US 2007/0091305 A1    Apr. 26, 2007

Related U.S. Application Data

(60) Provisional application No. 60/760,189, filed on Jan. 19, 2006, provisional application No. 60/730,558, filed on Oct. 26, 2005.

(51) Int. Cl.
*G01J 3/44* (2006.01)
(52) U.S. Cl. .................................................. 356/301
(58) Field of Classification Search ............... None
See application file for complete search history.

(56) References Cited

U.S. PATENT DOCUMENTS 4,405,237 A   9/1983   Manuccia et al.
6,108,081 A   8/2000   Holtom et al.
6,356,381 B1 * 3/2002   Schade et al. ............... 359/326
6,781,690 B2 * 8/2004   Armstrong et al. ......... 356/301
6,798,507 B2   9/2004   Xie et al.
6,809,814 B2   10/2004  Xie et al.
6,934,020 B2   8/2005   Shimada
2005/0280827 A1 12/2005   Potma et al.

FOREIGN PATENT DOCUMENTS

GB    2408796    6/2005

OTHER PUBLICATIONS

Oudar et al. "Polarization-Sensitive Coherent Anti-Stokes Raman Spectroscopy," Applied Physics Letters, Jun. 1979, pp. 758-760.

(Continued)

*Primary Examiner*—Tu T. Nguyen
(74) *Attorney, Agent, or Firm*—Gauthier & Connors LLP

(57) ABSTRACT

A system is disclosed for detecting a nonlinear coherent field induced in a sample. The system includes optics, a modulation system, and a detector system. The optics are for directing a first electromagnetic field at a first frequency $\omega_1$ and a second electromagnetic field at a second frequency $\omega_2$ toward a focal volume such that a difference frequency $\omega_1-\omega_2$ is resonant with a vibrational frequency of a sample in the focal volume. The modulation system is for modulating the difference frequency $\omega_1-\omega_2$ such that the difference frequency $\omega_1-\omega_2$ is tuned in and out of the vibrational frequency of the sample of at a modulation frequency. The detector system is for detecting an optical field that is generated through non-linear interaction of $\omega_1$ and $\omega_2$ and the sample responsive to the modulation frequency.

20 Claims, 9 Drawing Sheets

OTHER PUBLICATIONS

X.L. Nan et al., "Vibrational imaging of lipid droplts in live fibroblast cells with coherent anti-Stokes Raman scattering microscopy," J. Lipid Res. 44, 2003, pp. 2202-2208.

C.L. Evans et al., "Chemical imaging of tissue in vivo with video-rate coherent anti-Stokes Raman scattering (CARS) microscopy," Proc. Nat. Acad. Sci., USA, In press, 2005.

J.X. Cheng et al., "Polarization coherent anti-Stokes Raman scattering microscopy," Optic Letters, Sep. 2001, vol. 26, No. 17, pp. 1341-1343.

A. Volkmer et al., "Time-resolved coherent anti-Stokes Raman scattering microscopy: Imaging based on Raman free induction decay," Appl. Phys. Lett. 80, 2002, pp. 1505-1507.

E.O. Potma et al., "Heterodyne coherent anti-Stokes Raman scattering (CARS) imaging," Optic Letters, Jan. 2006, vol. 31, No. 2, pp. 241-243.

Akhmanov et al., "Coherent ellipsometry of Raman Scattering of Light," JETP Letters, 1977, vol. 25, pp. 416-420.

Born and Wolf, Principles of Optics, Pergaman Press, 1989, pp. 435-449.

J.X. Cheng et al., "An epi-detected coherent anti-Stokes Raman scattering (E-CARS) microscope with high resolution and high sensitivity," J. Phys. Chem. B 105, 2001, pp. 1277-1280.

Lotem, "Frequency modulation coherent anti-stokes Raman spectroscopy (FM-CARS): A Novel sensitive non-linear optical method" 1983 American Institute of Physics, J. Chem Phys. 79(5), Sep. 1, 1983, pp. 2177-2180.

Hayazawa et al., "Amplification of coherent anto-stokes Raman scattering by a metallic nanostructure for a high resolution vibration microscopy" Journal of Applied Physics, vol. 95, No. 5, Mar. 1, 2004, pp. 2676-2680.

Greve et al., "Gated heterodyne coherent anti-stokes Raman scattering with phase-locked tunable femtosecond pulses" 2005 Conference on Lasers & Electro-Optics pp. 1766-1768.

Vinegoni et al., "Nonlinear optical contrast enhancement for optical coherence tomography" Optics Express, Jan. 26, 2004, vol. 21, No. 2.

Zheltikov, "Limiting Temporal and Spectral Resolution in Spectroscopy and Microscopy of Coherent Raman Scattering with Chirped Ultrashort Laser Pulses" Journal of Experimental and Theoretical Physics, vol. 100, No. 5, pp. 833-843.

Cheng et al., "Coherent Anti-Stokes Raman Scattering Correlation Spectroscopy: Probing Dynamical Processes with Chemical Selectivity" J. Phys. Chem. A. 2002, 106, pp. 8561-8568.

Potma et al., "High-sensitivity coherent anti-Stokes Raman scattering microscopy with two tightly synchronized picosecond lasers" Optics Letters, vol. 27, No. 13, Jul. 1, 2002, pp. 1168-1170.

* cited by examiner $2\omega_p - \omega_s = \omega_{as}$

US 7,352,458 B2

SYSTEM AND METHOD FOR HIGH SENSITIVITY VIBRATIONAL IMAGING WITH FREQUENCY MODULATION COHERENT ANTI-STOKES RAMAN SCATTERING ANALYSES

PRIORITY

The present application claims priority to U.S. Provisional Patent Application Ser. No. 60/730,558 filed Oct. 26, 2005 as well as U.S. Provisional Patent Application Ser. Ser. No. 60/760,189 filed Jan. 19, 2006.

This invention was sponsored by NIH grants OD000277 and GM062536 and the government has certain rights to this invention.

BACKGROUND

The invention relates to the field of microscopy, and particularly related to the field of coherent anti-stokes Raman scattering microscopy.

Coherent anti-stokes Raman scattering (CARS) microscopy provides for the imaging of chemical and biological samples by using molecular vibrations as a contrast mechanism. In particular, CARS microscopy typically uses two laser fields, a pump electromagnetic field with a center frequency at $\omega_p$ and a Stokes electromagnetic field with a center frequency at $\omega_s$. The pump and stokes fields interact with a sample and generate a coherent anti-Stokes field having a frequency of $\omega_{AS}=2\omega_p-\omega_s$ in the phase matched direction. When the Raman shift of $\omega_p-\omega_s$ is tuned to be resonant at a given vibrational mode, an enhanced CARS signal is observed at the anti-Stokes frequency $\omega_{AS}$.

Unlike fluorescence microscopy, CARS microscopy does not require the use of fluorophores (which may undergo photobleaching), since the imaging relies on the vibrational contrast of biological and chemical materials. Further, the coherent nature of CARS microscopy offers significantly higher sensitivity than spontaneous Raman microscopy. This permits the use of lower average excitation powers (which is tolerable for biological samples). The fact that $\omega_{AS}>\omega_p, \omega_s$ allows the signal to be detected in the presence of one-photon background fluorescence. CARS microscopy provides information about the intrinsic vibrational resonances of a sample with high sensitivity, allowing for label-free, chemically-specific imaging.

For example, U.S. Pat. No. 4,405,237 discloses a coherent anti-Stokes Raman spectroscopic imaging device in which two laser pulse trains of different wavelengths, temporally and spatially overlapped, are used to simultaneously illuminate a sample. The '237 patent discloses a non-collinear geometry of the two laser beams and a detection of the signal beam in the phase matching direction with a two-dimensional detector.

U.S. Pat. No. 6,108,081 discloses a different method and apparatus for microscopic vibrational imaging using coherent anti-Stokes Raman scattering. In the apparatus of the '081 patent, collinear pump and Stokes beams were focused by a high numerical aperture (NA) objective lens. The nonlinear dependence of the signal on the excitation intensity ensures a small probe volume of the foci, allowing three-dimensional sectioning across a thick sample. The signal beam is detected in the forward direction.

There is also a nonresonant contribution to the CARS signal, however, that does not carry chemically-specific information that can distort and even overwhelm the resonant signal of interest. This nonresonant contribution provides background with no vibrational contrast from which the desired signal must be filtered or somehow distinguished. For example, a conventional lateral CARS intensity profile of a 535 nm polystyrene bead embedded in water includes a substantial amount of CARS background from water in addition to the characteristic CARS signal from the bead. The presence of this background from the isotropic bulk water has hindered efforts to increase the sensitivity of CARS imaging, particularly in biological applications. The CARS background is caused by electronic contributions to the third order nonlinear susceptibility. There exists a non-resonant contribution to the CARS signal of the sample of interest as well as of the surrounding isotropic bulk medium (i.e., solvent), which is independent of the Raman shift, $\omega_p-\omega_s$.

One approach to reducing the non-resonant background field in CARS spectroscopy is to take advantage of the fact that the non-resonant background has different polarization properties than the resonant signal. For example, see *Polarization-Sensitive Coherent Anti-Stokes Raman Spectroscopy*, by Oudar, Smith and Shen, Applied Physics Letters, June 1979, pp. 758–760 (1979); and *Coherent ellipsometry of Raman Scattering of Light*, by Akhmanov, Bunkin, Ivanov and Koroteev, JETP Letters, Vol. 25, pp. 416–420 (1977), which employ non-collinear excitation beams with different polarization directions.

U.S. Pat. No. 6,798,507 discloses a system in which the pump and Stokes beams are polarized, and a polarization sensitive detector is employed. In high resolution CARS microscopy, however, tightly focused collinear excitation beams are sometimes necessary. It is known that tightly focusing polarized beams will result in polarization scrambling. See *Principles of Optics*, Born and Wolf, Pergaman Press, 1989, pp. 435–449.

U.S. Pat. No. 6,809,814 discloses a system in which a CARS signal is received in the reverse direction (epi-direction) from the sample. The epi directed signal, however, is significantly smaller than the forward directed signal, and a stronger signal may be desired for certain applications.

There is a need, therefore, for a system and method for providing improved sensitivity of CAS microscopy for certain applications, and in particular, to provide a CARS detection scheme that reduces the non-resonant background hence yields a higher signal-to-background ratio.

SUMMARY

In accordance with an embodiment, the invention provides a system for detecting a nonlinear coherent field induced in a sample, said system. The system includes optics, a modulation system, and a detector system. The optics are for directing a first electromagnetic field at a first frequency $\omega_1$ and a second electromagnetic field at a second frequency $\omega_2$ towards a focal volume such that a difference frequency $\omega_1-\omega_2$ is resonant with a vibrational frequency of a sample in the focal volume. The modulation system is for modulating the difference frequency $\omega_1-\omega_2$ such that the difference frequency $\omega_1-\omega_2$ is tuned in and out of the vibrational frequency of the sample at a modulation frequency. The detector system is for detecting an optical field that is generated through non-linear interaction of $\omega_1$ and $\omega_2$ and the sample responsive to the modulation frequency.

In accordance with another embodiment of the invention, the system includes a source system, a modulation system, optics, and a detector system. The source system is for generating a first electromagnetic field at a first frequency, a second electromagnetic field at a second frequency that is different from said first frequency, and a third electromagnetic field at a third frequency that is different from the first frequency and different from the second frequency. The modulation system is for providing a modulated electromagnetic field that is switched between the second and third frequencies at a modulation frequency. The optics are for directing the first electromagnetic field and the modulated electromagnetic field toward a common focal volume. The detector system is for detecting a nonlinear coherent field that is generated responsive to the first and modulated electromagnetic fields in the focal volume.

In accordance with a further embodiment, the invention provides a method of detecting a nonlinear coherent field induced in a sample. The method includes the steps of directing a first electromagnetic field at a first frequency $\omega_1$ and a second electromagnetic field at a second frequency $\omega_2$ toward a focal volume such that a difference frequency $\omega_1-\omega_2$ is resonant with a vibrational frequency of a sample in the focal volume, modulating the different frequency $\omega_1-\omega_2$ such that the difference frequency $\omega_1-\omega_2$ is tuned in and out of the vibrational frequency of the sample at a modulation frequency, and detecting an optical field that is generated through non-linear interaction of $\omega_1$ and $\omega_2$ and the sample responsive to the modulation frequency.

BRIEF DESCRIPTION OF THE ILLUSTRATION EMBODIMENTS

The following description may be further understood with reference to the accompanying drawings in which.

Figure 8A:
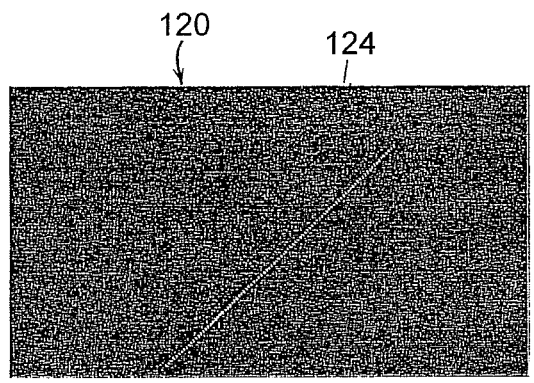
FIG. 8A shows an illustrative diagrammatic representation of a CARS microscopy image of 360 nm diameter polysterene beads taken using a forward CARS microscopy system.
Figure 8C:
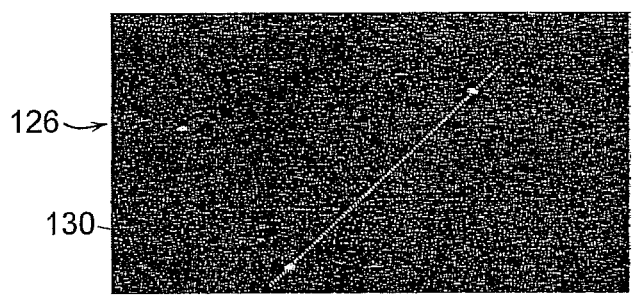
FIG. 8C shows an illustrative diagrammatic representation of a CARS microscopy image of the 360 nm diameter polysterene beads taken using a forward CARS microscopy system in accordance with an embodiment of the invention.
Figure 8E:
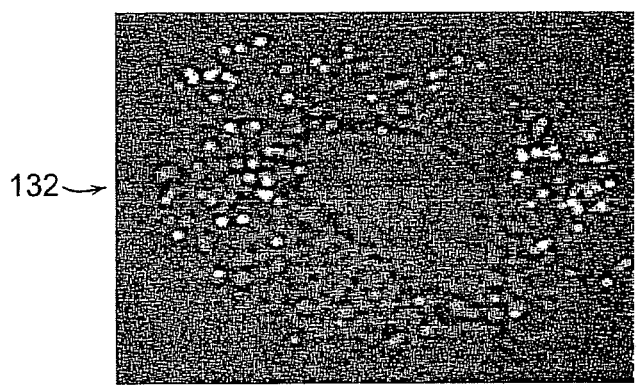
FIG. 8B is a graphic representation of the intensity of the image shown in FIG. 8A taken along a section thereof.
FIG. 8D is a graphical representation of the intensity of the image shown in FIG. 8B taken along a section thereof.
Figure 8F:
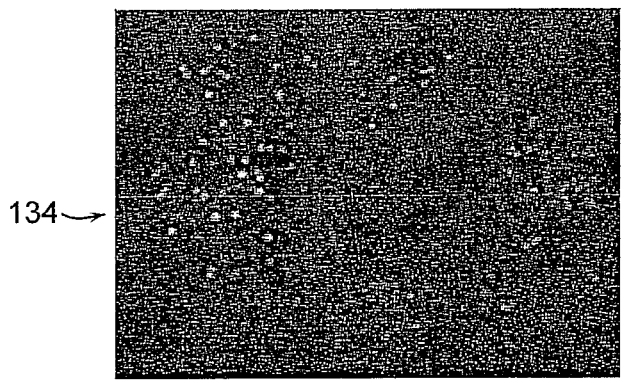
Figure 8B:
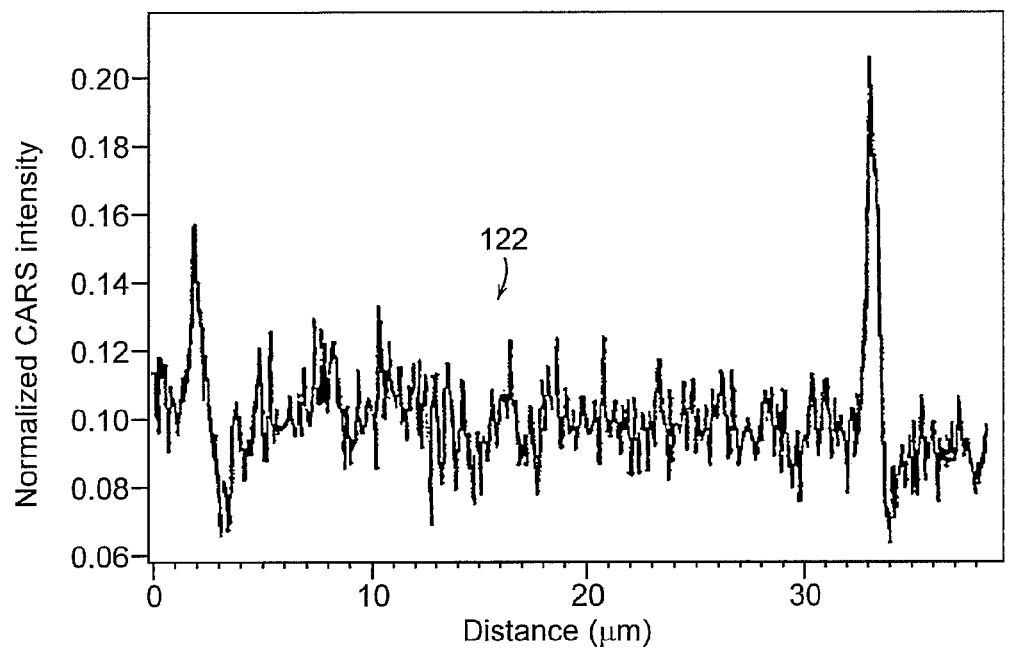
Figure 8D:
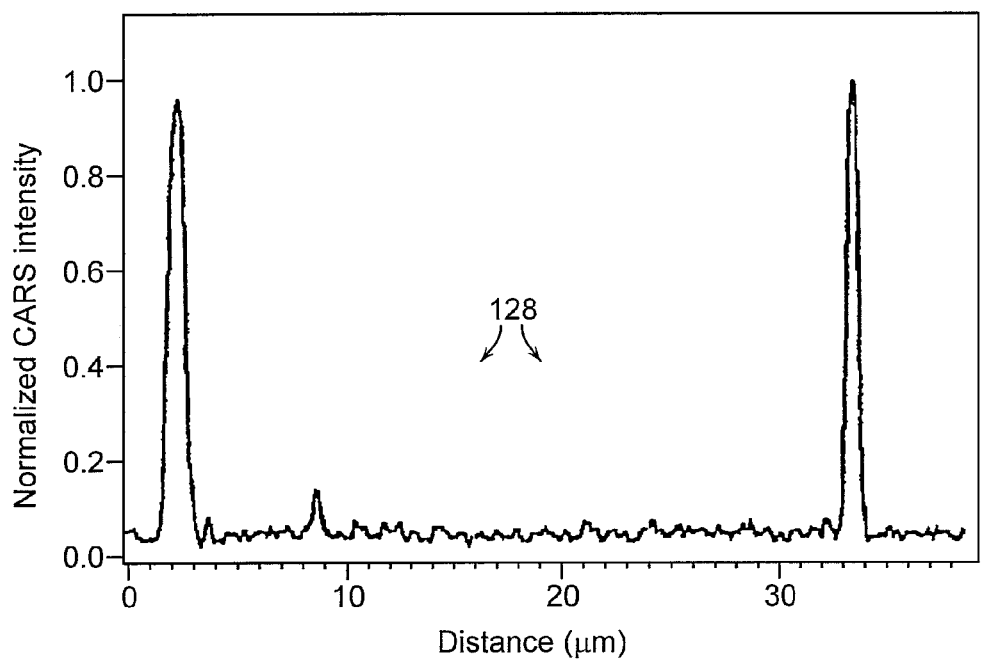
Figure 9:
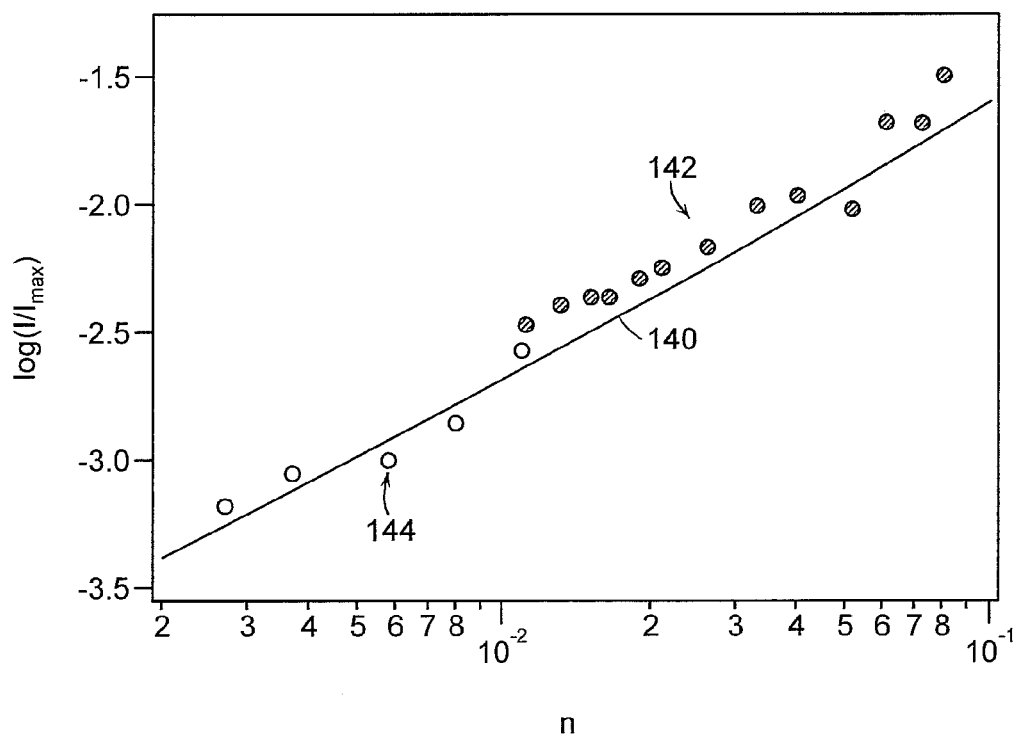

FIG. 8E shows an illustrative diagrammatic representation of a cell using the CARS system employed in FIGS. 8A and 8B, and FIG. 8F shows an illustrative diagrammatic representation of a cell using the CARS system employed in FIGS. 8C and 8D in accordance with an embodiment of the invention; and FIG. 9 shows an illustrative graphical representation of measured values of CARS signals in a microscopy system in accordance with an embodiment of the invention.

The drawings are shown for illustrative purposes only.

DETAILED DESCRIPTION

The invention involves performing CARS microscopy such that the frequency difference $\omega_1-\omega_2$ is rapidly changed to and from the frequency of a desired molecular vibration. In accordance with an embodiment, the Stokes beam is maintained at a fixed optical frequency and the optical frequency of the pump beam is rapidly switched to modulate the frequency difference. In another embodiment, the optical frequency of the Stokes beam may be rapidly modulated while the pump beam is maintained at an optical fixed frequency. In further embodiments, the optical frequency of both the Stokes beam and the pump beam may be rapidly switched to produce a modulated frequency difference.

CARS microscopy systems of various embodiments of the invention, therefore, provide significant increases in the detection sensitivity because non-resonant background information is suppressed by locking into the switching periodicity of the modulated frequency difference. CARS signals are generated by collinearly overlapped, tightly focused, and raster scanned pump and Stokes laser beams, whose difference in frequency is rapidly modulated. The resulting CARS signal is detected by a detector system that is response to the modulation frequency. This scheme efficiently suppresses the nonresonant background and allows for the detection of far fewer vibrational oscillators than possible though existing CARS microscopy methods.

Figure 1:
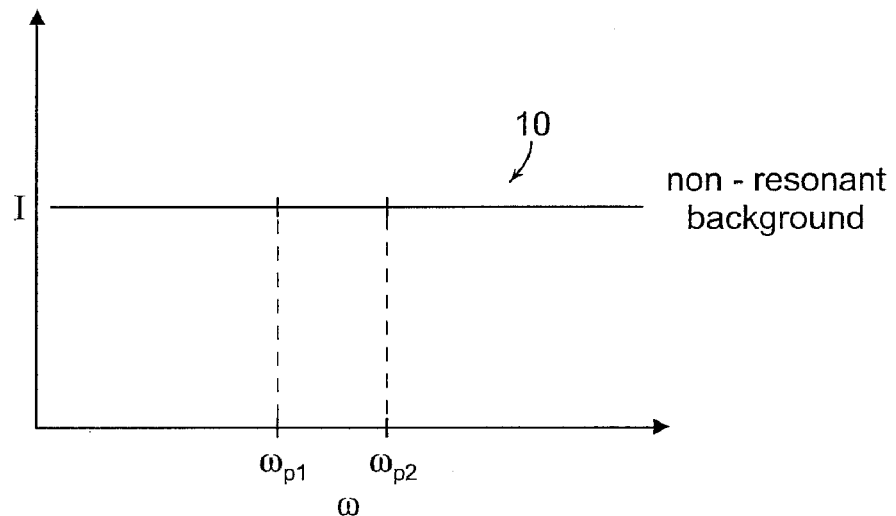
FIG. 1 shows a graphical representation of the frequency dependence of the non-resonant background signal in a CARS system.
Figure 2:
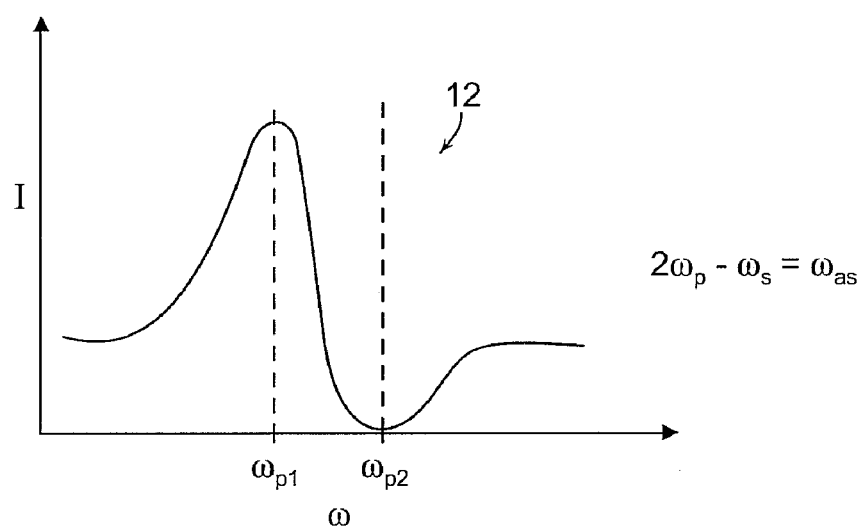
FIG. 2 shows a graphical representation of the frequency dependence of a resonant signal in a CARS system.

If the anti-Stokes signal that is obtained changes when the frequency difference is modulated, then it is known that the signal is due to a vibrational resonance. The nonresonant background, which will not change when the frequency difference is modulated, is therefore easily subtracted from the received anti-Stokes signal. With reference to FIG. 1, when the pump beam is modulated between $\omega_{p1}$ and $\omega_{p2}$ the non-resonant background remains the same as shown at 10, but the resonant sample being probed provides a response that very strongly correlates with the modulation frequency as shown at 12 in FIG. 2. The modulation frequency may be for example, about 500 kHz or higher. This frequency is faster than any noise that may be seen in the laser as laser noise occur generally below 10 kilohertz.

Figure 3:
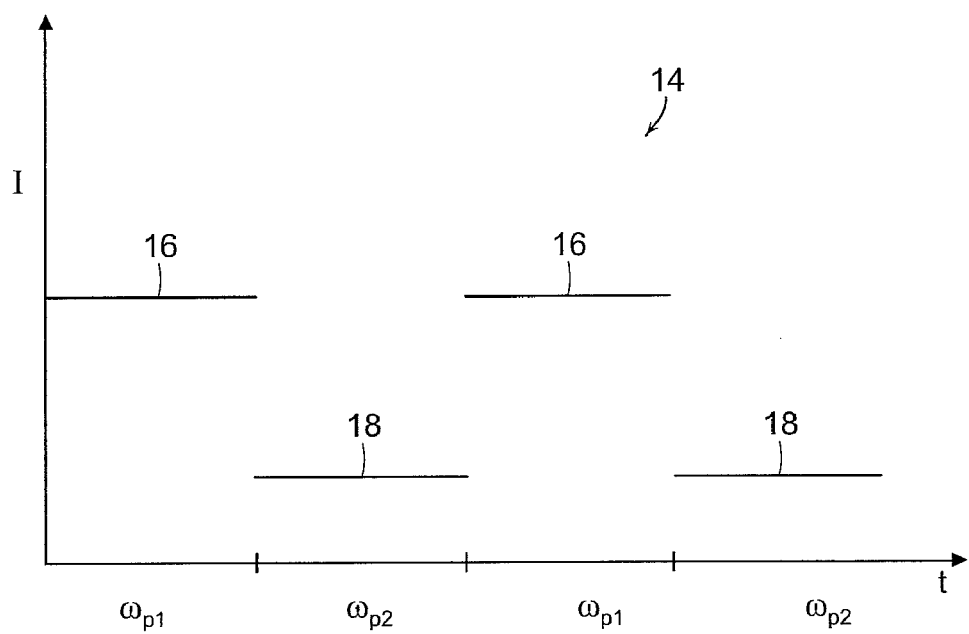
FIG. 3 shows a graphical representation of a switching output signal in a CARS system in accordance with an embodiment of the invention.

The output signal may be passed through a lock-in amplifier to provide that only changes at the time scale of the modulation period are provided in the final output. In accordance with other embodiments, an RF modulator/demodulator may be employed. For example, as shown at 14 in FIG. 3, the desired signal 16 is easily separated from the non-resonant background signal 18 by locking into signal components that change at the frequency of the modulation. The invention provides that the noise in the background may be much more significantly suppressed that with conventional CARS systems. The improved sensitivity may permit viewing of molecules in cells at micromolar concentrations.

The CARS response originates from the third order nonlinear susceptibility, which is the sum of a resonant contribution, $$\chi_R^{(3)}(\Omega),$$

and a nonresonant electronic component, $$\chi_{NR}^{(3)}.$$

The total detected CARS signal is given by:

$$I_{CARS}(\Omega) \propto |\chi_R^{(3)}(\Omega) + \chi_{NR}^{(3)}|^2 = |\chi_R^{(3)}(\Omega)|^2 + (\chi_{NR}^{(3)})^2 + 2\mathrm{Re}\{\chi_R^{(3)}(\Omega)\}\chi_{NR}^{(3)} \quad (1)$$

Figure 4A:
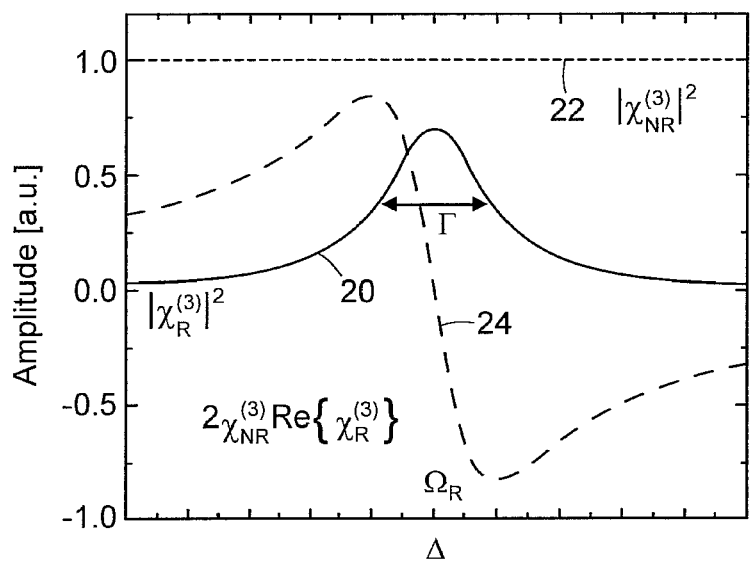
FIG. 4A shows a graphical representation of an isolated resonance for components of a CARS signal in a system probed with a narrow band source.

The frequency dependence of the three terms $$|\chi_R^{(3)}(\Omega)|^2, (\chi_{NR}^{(3)})^2,$$

and $$2\mathrm{Re}\{\chi_R^{(3)}(\Omega)\}\chi_{NR}^{(3)}$$

are shown at 20, 22 and 24 respectively in FIG. 4A. The three terms are plotted versus detuning $\Delta = \omega_p - \omega_s - \Omega_R$, where $\Omega_R$ is the center frequency of a homogenously broadened Raman line with bandwidth $\Gamma$. The solid line 20 is the purely resonant CARS signal component. The dotted line 22 is the spectrally-independent CARS signal component due to the nonresonant third order nonlinearity $$\chi_{NR}^{(3)}.$$

The dashed line 24 represents the heterodyne component of Equation (1). The curves are calculated with an assumption that $$\chi_{NR}^{(3)} = 1.2 \times \chi_R^{(3)}(\Delta = 0).$$

The nonresonant term can often obscure the resonant CARS signal of interest, making it difficult to identify the chemically selective contributions to an image. This is especially true when imaging biological materials as the aqueous environment gives rise to a substantial nonresonant response that often overwhelms the resonant signal.

Figure 4B:
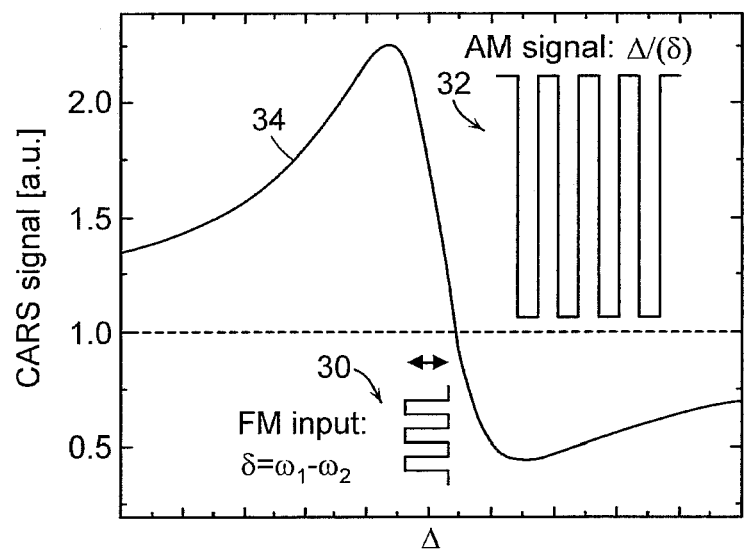
FIG. 4B shows a graphical representation of the sum of the contributions shown in FIG. 4A.

Consider an isolated resonance centered at vibrational frequency $\Omega_R$ with FWHM linewidth $\Gamma$ (as shown in FIG. 4A) probed with a narrow-band source. If the source is rapidly switched between two frequencies, $\omega_1$ and $\omega_2$, with a frequency difference $\delta = \omega_1 - \omega_3$ the frequency modulation results in an amplitude modulation of the CARS signal, $\Delta/(\delta) = I(\omega_1) - I(\omega_2)$ that can be extracted using phase-sensitive detection. FIG. 4B shows a schematic of such an FM-CARS process. The solid line 34 is the sum of the contributions from FIG. 4a. The Raman resonance probed by FM-CARS, therefore, acts as an FM-to-AM converter, resulting in an amplitude-modulated signal that can be detected by a lock-in amplifier. In this approach, a resonant spectral feature transforms from a frequency modulation (FM) to amplitude modulation (AM) as shown at 30 and 32 for the signal 34 as shown in FIG. 4B. The non-resonant contribution, which is essentially spectrally flat, does not contribute to the detected modulated signal and therefore is efficiently suppressed.

When the concentration of resonant species in a sample is high under this suppression conditions, the quadratic term $$|\chi_R^{(3)}(\Omega)|^2$$

in Equation 1 is the greatest contribution to the detected signal. At much lower concentrations, however, the linear term $$2\mathrm{Re}\{\chi_R^{(3)}(\Omega)\}\chi_{NR}^{(3)}$$

in Equation 1 becomes dominant. This heterodyne term contains a factor of $$\chi_{NR}^{(3)},$$

which implies that the component can be effectively enhanced by the nonresonant response of the solvent. The above approach is implemented by modulating the optical frequency of the pump beam $\omega_p$, at a high enough rate (>500 kHz) to separate the modulated signal from the lower frequency laser noise. The modulation frequency may depend on the particular laser source that is employed. A value may be set to be far from the noise spectrum peak of the laser (relaxation resonance frequency) as well as characteristic mechanical resonance frequencies of the beam steering and laser resonator optics.

Figure 5:
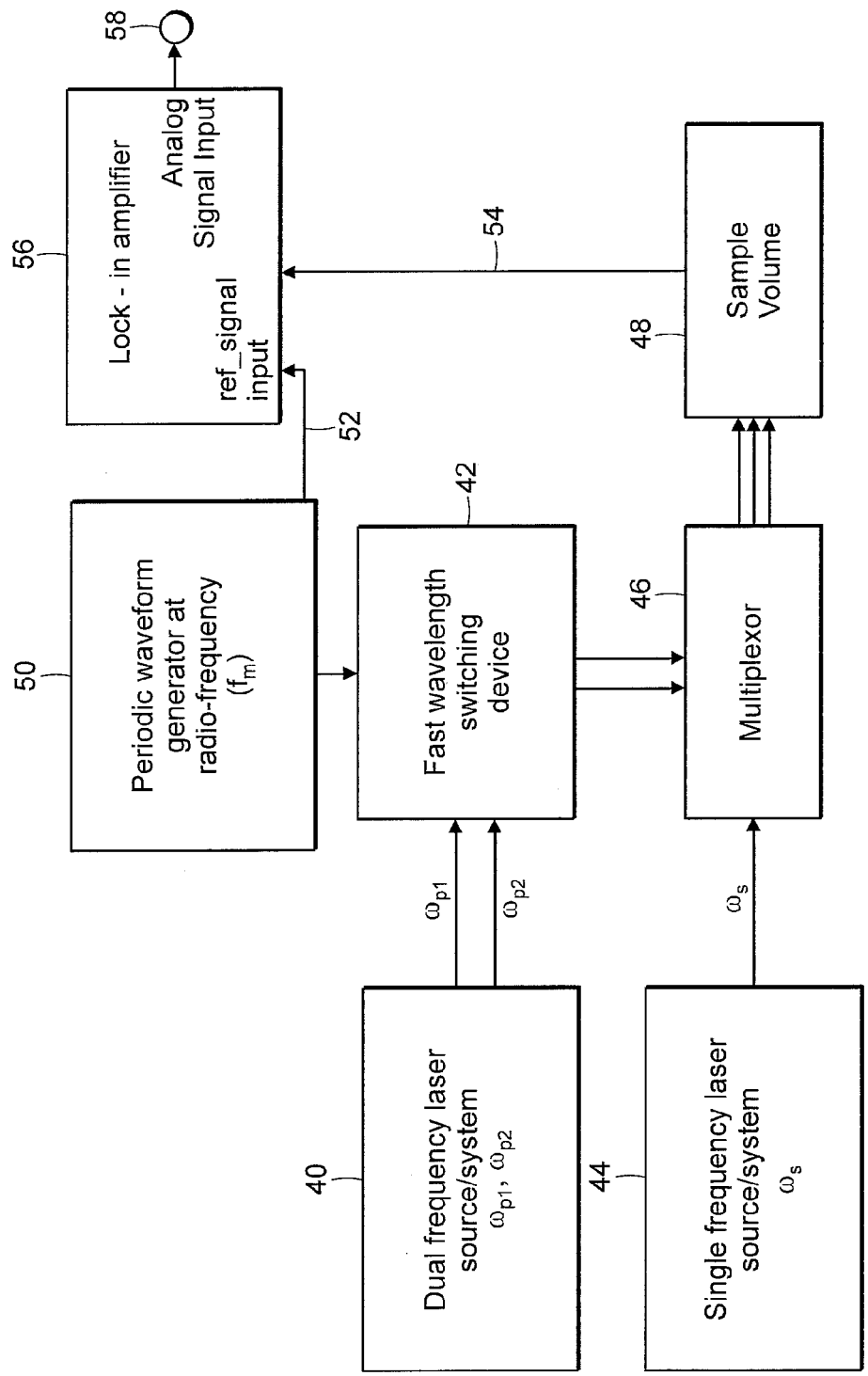
FIG. 5 shows an illustrative diagrammatic functional view of a system in accordance with an embodiment of the invention.

As shown in FIG. 5, a system in accordance with an embodiment of the invention includes a dual frequency laser source or system 40 that provides the two pump beams $\omega_{p1}$ and $\omega_{p2}$ to a fast wavelength switching device 42. The two switched beams $\omega_{p1}$ and $\omega_{p2}$ are then directed to a multiplexor 46 together with a Stokes beam $\omega_s$ from a single frequency laser source 44. The three beams $\omega_{p1}$, $\omega_{p2}$ and $\omega_S$ are then directed toward a sample volume 48 for either microscopy or spectroscopy. The fast wavelength switching device 42 also receives a modulation frequency signal ($f_m$) at radio-frequency from a periodic waveform generator 50. The waveform generator 50 also provides a reference input signal 52 to a lock-in amplifier 56. The lock-in amplifier 56 also receives the CARS signal 54 from the sample volume 48, and identifies only the part of the signal 54 that is at the same frequency as and in phase with the reference input signal 52. The portion of the signal 54 that results from the sample and not the background is then provided to an output node 58. The system, therefore, is able to remove background information by isolating the amplitude modulated and anti-Stokes signal.

Figure 6:
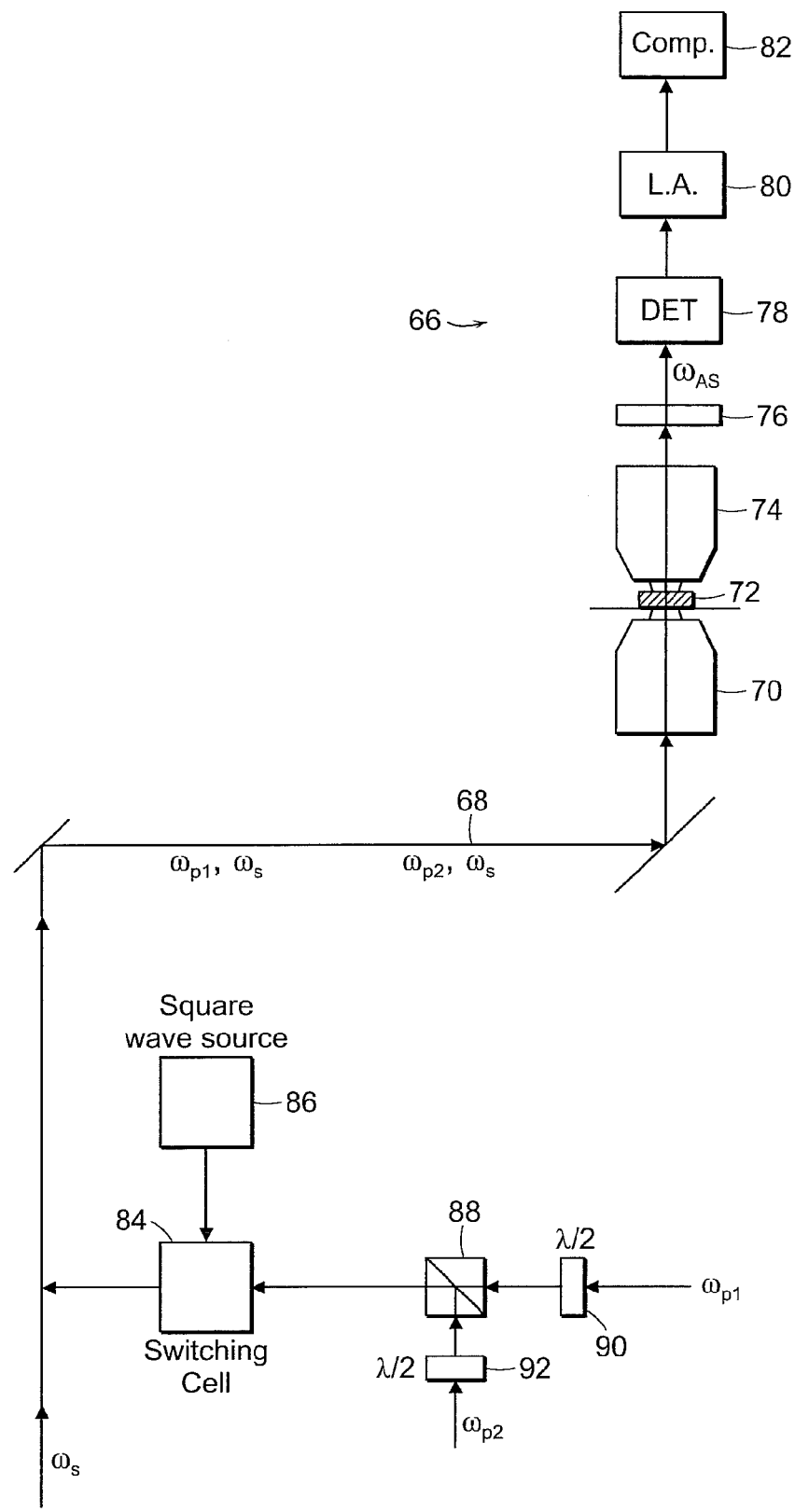
FIG. 6 shows an illustrative diagrammatic view of a CARS microscopy system in accordance with an embodiment of the invention.

As shown in FIG. 6, a CARS microscopy system 66 may receive a Stokes beam together with modulated pump beams 68 that are directed to a microscope objective lens 70, and onto a sample 72. The CARS signal is detected in the forward direction, and is received by collecting optics 74, filtered by one or more filters 76, detected by a detector 78, passed through a lock-in-amplifier 80, and directed toward a computer 82. The modulated pump beam is provided to a switching unit 84 that combines the modulated pump beam with the Stokes beam. The unit 84 receives a square wave from a square wave source 86, and receives combined $\omega_{p1}$ and $\omega_{p2}$ signals that have been combined at a polarizing beam splitter 88 after being passed through half-wave plates 90 and 92 as shown.

Figure 7A:
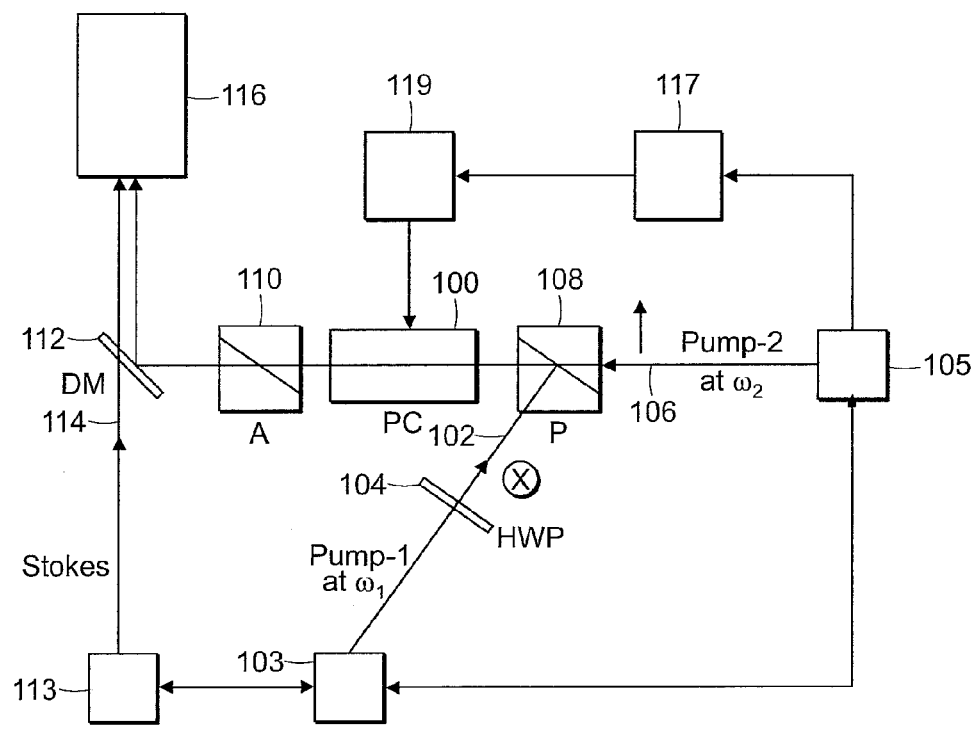
FIGS. 7A and 7B show illustrative diagrammatic views of switching systems for a CARS microscopy or spectroscopy systems in accordance with different embodiments of the invention.

As shown in FIG. 7A a switching system for a pulsed CARS system in accordance with a particular embodiment of the invention includes a Pockel's cell 100 that receives a first pump beam $\omega_{p1}$ 102 through a half wave plate 104, and a second pump beam $\omega_{p2}$ 106 through a beam splitter/combiner 108. The output of the Pockel's cell 100 is provided to a Glan-Taylor prism 110 and then to a dichroic mirror 112 where it is combined with a Stokes beam 114. The Stokes and pump beams (which may be combined to be collinear) are then directed toward a microscope (including, for example, elements 70–82 shown in FIG. 6) or spectrometer 116. The system of FIG. 7A also includes a synchronization system by which the sources 103, 105 and 113 for producing the signals 104, 106 and 114 respectively, are synchronous with one another, and a synchronous signal is provided to a frequency divider 117. The frequency divider 117 is then coupled to a waveform generator 119 that provides a modulation signal that is then synchronized with the pump and stokes signals 104, 106 and 114. At least one of the Stokes or pump beams is modulated such that the difference frequency is tuned in and out of the vibrational frequency of the sample at the modulation frequency.

Figure 7B:
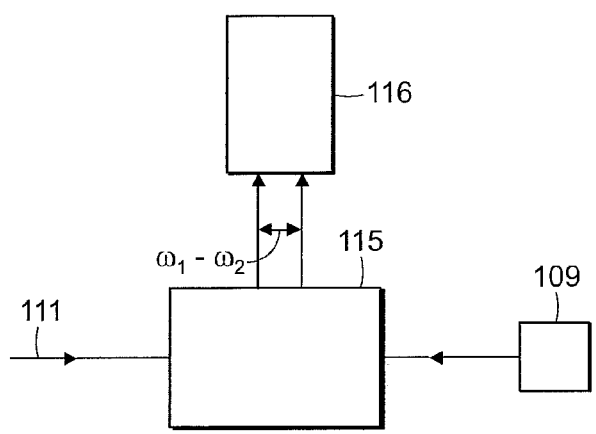

As shown in FIG. 7B, a switching system for a pulsed or CW CARS microscopy or spectroscopy system 116 may include a dual wavelength source 115 that receives an input signal 111 (e.g., pulsed or CW) and a modulation input 109 (that may for example modulate the duel wavelength source 115 or change the temperature or orientation of a non-linear crystal an optical parametric oscillator 115). In any event, the difference frequency between the two outputs (which may be combined to be colinear), is modulated such that the difference frequency $\omega_1-\omega_2$ is tuned in and out of the vibrational frequency of the sample at the modulation frequency. In accordance with further embodiments, the system may also include a third source for providing a third electromagnetic field at a third frequency $\omega_3$ that may be used to probe the sample at a desired probing frequency.

In accordance with an embodiment of the invention, three pulsed lasers are coupled into a modified laser-scanning microscope (Olympus, FV300). The Stokes beam is about 10% of the output from a passively mode-locked, fixed-frequency Nd:YVO$_4$ laser (High-Q, picoTRAIN, 7 ps, 1064 nm, 76 MHz rep. rate). The 90% output of the Nd:YVO$_4$ source is used to synchronously pump an intracavity doubled optical parametric oscillator (OPO) producing tunable 5 ps near-IR radiation for use as a pump beam (Pump-1). The second pump beam (Pump-2) is provided by a mode-locked Ti:Al$_2$O$_3$ oscillator delivering tunable 3 ps pulses that are electronically synchronized to the Nd:YVO$_4$ source. A half-wave plate inserted into the Pump-1 beam path is used to rotate the polarization so that Pump-1 and Pump-2 are perpendicularly polarized. The two pump beams are then combined in a two-port Glan-Taylor prism and sent collinearly into a Pockel's cell. Square waveforms with a 50% duty cycle, derived from a pulse delay generator synchronized to the laser pulse train, supply a modulation signal at a frequency of ~500 kHz to the Pockel's cell. When the waveform is in the low state, Pump-1 is allowed to pass through the exit analyzer. When the waveform is in the high state, the polarization of both beams is rotated by $\pi/2$, such that Pump-2 now passes unattenuated though the analyzer while Pump-1 is blocked. This arrangement provides the rapid wavelength modulation needed for the experiment. The modulated pump beams are spatially combined with the Stokes beam on a dichroic mirror and the combined beams are directed into the scanning microscope. The CARS signal from the sample is detected by a PMT and fed into a lock-in amplifier. The lock-in reference is provided by the external signal supplied from the pulse generator driving the Pockel's cell. The half-wave plate introduced into the Pump-1 beam path can be used in conjunction with the Glan-Taylor prism to balance the intensity of the two beams for maximum nonresonant signal suppression.

FIG. 8A shows at 120 a CARS microscopy image of 360 nm diameter polysterene beads on a glass surface taken at $\Delta$ equal to about 3050 cm$^{-1}$, and FIG. 8B shows at 122 a graphical representation of the intensity profile along section 124 of FIG. 8A. FIG. 8C shows at 126 a CARS microscopy image of the 360 nm diameter polysterene beads in a frequency modulated (FM) CARS system in accordance with an embodiment of the invention, and FIG. 8D shows at 128 a graphical representation of the intensity profile along section 130 of FIG. 8C. Pump-1 is tuned to the peak of the vinyl CH stretching band at 3050 cm$^{-1}$ while Pump-2 targets the spectrally flat region at 3000 cm$^{-1}$.

As shown in FIG. 8B, the resonant signal is only slightly stronger than that of the nonresonant background. The same image acquired using the FM-CARS technique in accordance with an embodiment of the invention demonstrates considerable suppression of the nonresonant background as shown in FIG. 8D. The improvement in signal-to-background ratio is shown in the intensity profiles through the beams (FIGS. 8B and 8D). The nonresonant signal suppression of FM-CARS is immediately applicable to in vivo imaging, where nonresonant CARS signals can be as strong as the resonant signal of interest.

FIG. 8E shows at 132 a CARS image are of a fixed A549 human lung cancer cell cultured with deuterium-labeled oleic acids taken at $\Delta=2100$ cm$^{-1}$, and FIG. 8F shows the same sample as FIG. 8E taken at $\Delta=2100$ cm$^{-1}$ obtained when modulating between 2060 cm$^{-1}$ and 2100 cm$^{-1}$ in accordance with an embodiment of the invention. Nonresonant features in the cell have been completely suppressed, leaving only deuterium-rich cellular structures visible. Note that the nonresonant background has been significantly reduced by the FM-CARS method. The cell was cultured with deuterated oleic acid before fixation and imaged at the CD$_2$ stretching frequency (Pump-1: 2100 cm$^{-1}$) and at an off-resonance frequency (Pump-2: 2060 cm$^{-1}$). The normal forward-CARS image (FIG. 8E), taken at a Raman shift of 2100 cm$^{-1}$, exhibits many nonresonant cellular features that make it unclear which cellular components contain the deuterated compound. When FM-CARS is used to image the cell (FIG. 8F) the nonresonant signals vanish, revealing only the resonant signals of the deuterated lipid droplets.

In addition to truly resonant imaging, FM-CARS also allows for increased detection sensitivity over conventional CARS microscopy. To quantify the increased sensitivity, solutions of methanol dissolved in water were used. Methanol is well characterized by Raman spectroscopy and contains only a single $CH_3$ moiety that gives rise to two relatively narrow ($\Gamma_{FWHM}$ equal to about 25 cm$^{-1}$), well-spaced Lorentzian-like peaks in the CH stretching region. For this experiment, Pump-1 was tuned to target 2928 cm$^{-1}$, which corresponds to the symmetric $CH_3$ stretch of methanol, while Pump-2 was tuned to target 3048 cm$^{-1}$ were there is no vibrational resonance. As considered earlier, the FM-CARS intensity in terms of detuning ($\Delta_{1,2}=\omega_{p1,p2}-\omega_s-\Omega$) is equal to $\Delta I(\delta)=I(\Delta_1)-I(\Delta_2)$. At relatively low concentrations, $I(\Delta_{1,2})$ can be expressed in terms of the fraction of maximum solute concentration, n, by the following equation.

$$I_{CARS}(\Delta, n) = I_{CARS}^{H_2O} \left[ \frac{\left(\frac{\Gamma}{2}\right)^2}{\Delta^2 + \left(\frac{\Gamma}{2}\right)^2} \right] \left( Rn^2 - 2\sqrt{R}\left(\frac{2\Delta}{\Gamma}\right)n \right) \quad (2)$$

where $$I_{CARS}^{H_2O}$$

is the nonresonant CARS intensity from pure water, and R is the ratio of peak CARS signal from pure method to $$I_{CARS}^{H_2O}.$$

The FM-CARS signal is maximized at $$\Delta_{1,2} = \pm\frac{\Gamma}{2}.$$

The R parameter can be readily measured experimentally at the resonance maximum, which is R=24 for this experiment.

FIG. 9 presents the experimentally measured values of the FM-CARS microscopy signal versus concentration for two distinctly different lock-in detection bandwidths. As shown at 140 in FIG. 9 equation (2) above may be plotted as concentration (n) versus the log of (Intensity/Intensity$_{max}$). The signal intensity is from methanol dissolved in water while $I_{max}$ is the CARS signal intensity from a pure methanol sample. The filled circles (as shown at 142) represent the experimental data points taken at the detector bandwidth is 25 KHz. The open circles (as shown in 144) corresponds to data taken when the detector bandwidth was set to 1.6 Hz.

Since FM-CARS makes use of a lock-in amplifier, the noise floor for the detected resonant signal may be reduced by narrowing the detector bandwidth to achieve better resonant signal detection sensitivity, with the ultimate sensitivity reached at an infinitely narrow bandwidth. While a detection bandwidth of $f_1$=25 kHz (filled circles) achieves significantly better sensitivity than seen in normal CARS, the ultimate sensitivity of our configuration is reached at a bandwidth of $f_2$=1.6Hz (open circles). The equation (2) relationship (solid line) shown at 140 provides a direct fit to the data. The efficient removal of nonresonant background originating from water with a narrow detection bandwidth ($f_2$) allowed the detection of resonant signal from methanol with only 5×10$^5$ oscillators in the probed volume of 100 attoliters, as opposed to approximately 4×10$^8$ oscillators achieved with normal forward-CARS in the same experiment. The minimum detectable signal for both bandwidths differs from the expected value since they should scale linearly with the bandwidth (f). This suggests that the CARS signal noise spectrum has significant components in sub-Hz region, which most likely originate from beam pointing instability as well as laser intensity and spatial mode fluctuations.

Improvements to this technique, including dual-wavelength laser sources, OPOs with fast electro-optic tuning, and acousto-optic tunable filters for rapid wavelength modulation will very likely improve the detection limit by eliminating sources of noise. Systems of the invention may also be used to detect small changes in a vibrational band through appropriate choice of the modulated wavelengths.

In various embodiments, therefore, the invention provides a method for CARS microscopy that involves the efficient suppression of nonresonant signals based on rapid modulation of the difference frequency between the pump and Stokes beams. This approach vastly enhances the ability to distinguish resonant features from the nonresonant background, providing resonant images with an improvement of nearly three orders of magnitude in sensitivity for chemical species at low concentrations.

The invention claimed is:

1. A system for detecting a nonlinear coherent field induced in a sample, said system comprising:
   optics for directing a first electromagnetic field at a first frequency $\omega_1$ and a second electromagnetic field at a second frequency $\omega_2$ toward a focal volume such that a difference frequency $\omega_1-\omega_2$ is resonant with a vibrational frequency of a sample in the focal volume;
   modulation means for modulating the difference frequency $\omega_1-\omega_2$ such that the difference frequency $\omega_1-\omega_2$ is tuned in and out of the vibrational frequency of the sample at a modulation frequency; and
   detector means for detecting an optical field that is generated through non-linear interaction of $\omega_1$ and $\omega_2$ and the sample responsive to the modulation frequency.

2. The system as claimed in claim 1, wherein said first frequency is a pump frequency and said second frequency is a Stokes frequency for a CARS system.

3. The system as claimed in claim 1, wherein the modulation frequency is between about 500 kHz and about 5000 kHz.

4. The system as claimed in claim 1, wherein said system further includes a periodic waveform generator that generates a modulation signal at the modulation frequency.

5. The system as claimed in claim 4, wherein said modulated signal is synchronous with at least one of said first and second electromagnetic fields.

6. The system as claimed in claim 1, wherein at least one of said first and second electromagnetic fields is modulated at the modulated frequency.

7. The system as claimed in claim 1, wherein both said first and second fields are modulated at said modulation frequency such that the difference frequency $\omega_1-\omega_2$ is tuned in and out of the vibrational frequency of the sample at the modulation frequency.

8. The system as claimed in claim 1, wherein said system further includes a third electromagnetic field for probing the sample.

9. The system as claimed in claim 1, wherein at least one of said first and second electromagnetic fields is generated by a dual wavelength source.

10. The system as claimed in claim 1, wherein said optical field that is generated through non-linear interaction of $\omega_1$ and $\omega_2$ and the sample responsive to the modulation frequency is generated at $2\omega_1-\omega_2$.

11. A system for detecting a nonlinear coherent field induced in a sample, said system comprising:
   a source system for generating a first electromagnetic field at a first frequency, a second electromagnetic field at a second frequency that is different from said first frequency, and a third electromagnetic field at a third frequency that is different from said first frequency and different from said second frequency;
   modulation means for providing a modulated electromagnetic field that is switched between said second and third frequencies at a modulation frequency;
   optics for directing said first electromagnetic field and said modulated electromagnetic field toward a common focal volume; and
   detector means for detecting a nonlinear coherent field that is generated responsive to said first and modulated electromagnetic fields in the focal volume.

12. The system as claimed in claim 11, wherein said first frequency is a pump frequency and said second and third frequencies are Stokes frequencies for a CARS system.

13. The system as claimed in claim 11, wherein said first frequency is a Stokes frequency and said second and third frequencies are pump frequencies for a CARS system.

14. The system as claimed in claim 11, wherein the modulation frequency is at least about 500 kHz.

15. The system as claimed in claim 11, wherein said system further includes a periodic waveform generator that generates a modulation signal at the modulation frequency.

16. The system as claimed in claim 15, wherein said periodic waveform generator is synchronized with said source system.

17. The system as claimed in claim 11, wherein at least one of said first and second electromagnetic fields is generated by a dual wavelength source.

18. A method of detecting a nonlinear coherent field induced in a sample, said method comprising the steps of:
   directing a first electromagnetic field at a first frequency $\omega_1$ and a second electromagnetic field at a second frequency $\omega_2$ toward a focal volume such that a difference frequency $\omega_1-\omega_2$ is resonant with a vibrational frequency of a sample in the focal volume;
   modulating the difference frequency $\omega_1-\omega_2$ such that the difference frequency $\omega_1-\omega_2$ is tuned in and out of the vibrational frequency of the sample at a modulation frequency;
   detecting an optical field that is generated through non-linear interaction of $\omega_1$ and $\omega_2$ and the sample responsive to the modulation frequency; and
   providing an output signal to a computer that is representative of the detected optical field that is generated through non-linear interaction of $\omega_1$ and $\omega_2$ such that coherent anti-Stokes Raman scattering analysis may be performed on the sample.

19. The method as claimed in claim 18, wherein said step of modulating the difference frequency involves modulating at least one of said first and second electromagnetic fields at the modulation frequency.

20. The method as claimed in claim 18, wherein said step of modulating the difference frequency involves modulating both said first and second fields at said modulation frequency such that the difference frequency $\omega_1-\omega_2$ is tuned in and out of the vibrational frequency of the sample at the modulation frequency.

* * * * *